United States Patent
Willis et al.

(10) Patent No.: US 6,579,460 B1
(45) Date of Patent: Jun. 17, 2003

(54) PROCESS AND COMPOSITION FOR REMOVING TOXINS FROM BODILY FLUIDS

(75) Inventors: Richard R. Willis, Cary, IL (US); David S. Bem, Arlington Heights, IL (US); Daniel L. Ellig, Arlington Heights, IL (US)

(73) Assignee: UOP LLC, Des Plaines, IL (US)

( * ) Notice: Subject to any disclaimer, the term of this patent is extended or adjusted under 35 U.S.C. 154(b) by 105 days.

(21) Appl. No.: 09/805,098

(22) Filed: Mar. 13, 2001

(51) Int. Cl.$^7$ ............................................. B01D 15/04
(52) U.S. Cl. ................. 210/638; 210/483; 210/510.1; 210/681; 210/691; 210/903; 210/907; 210/908; 210/669; 423/326; 423/331; 423/332; 423/592; 423/700; 435/2
(58) Field of Search ................. 210/638, 645, 210/646, 660, 669, 667, 681, 690, 502.1, 510.1, 691, 903, 906, 908, 909, 483; 435/2; 424/650; 423/326, 331, 332, 700, 701, 713, 592; 502/349, 350, 415

(56) References Cited

U.S. PATENT DOCUMENTS

| | | | |
|---|---|---|---|
| 3,274,124 A | * 9/1966 | O'Hara ....................... 252/451 |
| 3,617,545 A | * 11/1971 | Dubols et al. | |
| 3,909,450 A | * 9/1975 | O'Hara ....................... 252/438 |
| 4,247,393 A | * 1/1981 | Wallace ....................... 210/638 |
| 4,261,828 A | 4/1981 | Brunner et al. ............... 210/287 |
| 4,542,015 A | * 9/1985 | Smakman et al. ............. 424/79 |
| 4,581,141 A | 4/1986 | Ash ............................ 210/502 |
| 4,988,659 A | * 1/1991 | Pecoraro ...................... 502/235 |
| 5,536,412 A | 7/1996 | Ash ............................ 210/645 |
| 5,888,472 A | * 3/1999 | Bem et al. .................... 423/713 |
| 5,891,417 A | * 4/1999 | Bem et al. .................... 423/700 |
| 5,910,462 A | * 6/1999 | Gani et al. ..................... 501/80 |
| 6,099,737 A | * 8/2000 | Sherman et al. ............. 210/691 |
| 6,332,985 B1 | * 12/2001 | Sherman et al. ............. 210/638 |

FOREIGN PATENT DOCUMENTS

EP    0 046 971    10/1982

OTHER PUBLICATIONS

"Dialysate Regeneration" by A.J. Wing et al in "Replacement of Renal Function By Dialysis" edited by W. Drukker et al. (1986), pp. 323–340.*

* cited by examiner

Primary Examiner—John Kim
(74) Attorney, Agent, or Firm—John G. Tolomei; Frank S. Molinaro

(57) ABSTRACT

A process and a composite for removing toxic cations and anions from blood or dialysate is disclosed. The process involves contacting blood or dialysate with a shaped ion exchange composite to remove ammonium and phosphate ions. The composite is a mixture of an anion exchange composition such as zirconia and a microporous cation exchange composition formed into a shaped article and optionally containing a binder such as hydrous zirconium oxide. The microporous cation exchangers are represented by the following empirical formula.

$$A_pM_xZr_{1-x}Si_nGe_yO_m \quad (I)$$

or $$A_pM_xTi_{1-x}Si_nGe_yO_m \quad (II)$$

29 Claims, No Drawings

PROCESS AND COMPOSITION FOR REMOVING TOXINS FROM BODILY FLUIDS

FIELD OF THE INVENTION

The invention relates to a process and a composition for removing toxins from blood or dialysate solutions. The fluid is contacted with a combined cation and anion exchange composition to remove toxins such as ammonium cations and phosphate anions.

BACKGROUND OF THE INVENTION

In mammals, e.g., humans, when the kidneys and/or liver fail to remove metabolic waste products from the body, most of the other organs of the body also soon fail. Accordingly, extensive efforts have been made to discover safe and effective methods for removing toxins from patients' blood by extracorporeal treatment of the blood. Many methods have been proposed for removing small molecular toxins, protein-bound molecules or larger molecules thought to be responsible for the coma and illness of hepatic failure. Some of these toxic compounds have been identified as urea, creatinine, ammonia, phenols, mercaptans, short chain fatty acids, aromatic amino acids, false neural transmitters (octopamine), neural inhibitors (glutamate) and bile salts. Among these, phenols and mercaptans, along with bilirubin and bacterial endotoxins, also occur as strong protein-bound toxins and are thus more difficult to effectively remove from the blood. Middle molecular weight toxins having a molecular weight of about 300 to about 10,000 can also be present and are difficult to effectively remove.

The art shows a number of ways to treat blood containing such toxins. The classic method is of course dialysis. Dialysis is defined as the removal of substances from a liquid by diffusion across a semipermeable membrane into a second liquid. Dialysis of blood outside of the body (hemodialysis) is the basis of the "artificial kidney." The artificial kidney treatment procedure generally used today evolved from that developed by Kolff in the early 1940s.

Since the 1940s there have been a number of disclosures which deal with improvements on artificial kidneys or artificial livers. Thus, U.S. Pat. No. 4,261,828 B1 discloses an apparatus for the detoxification of blood. The apparatus comprises a housing filled with an adsorbent such as charcoal or a resin and optionally an enzyme carrier. In order to prevent direct contact between the blood and the adsorbent, the adsorbent may be coated with a coating which is permeable for the substances to be adsorbed yet prevent the direct contact between the corpuscular blood components and the adsorbents. U.S. Pat. No. 4,581,141 B1 discloses a composition for use in dialysis which contains a surface adsorptive substance, water, a suspending agent, urease, a calcium-loaded cation exchanger, an aliphatic carboxylic acid resin and a metabolizable organic acid buffer. The calcium loaded cation exchanger can be a calcium-exchanged zeolite. EP 0 046 971 A1 discloses that zeolite W can be used in hemodialysis to remove ammonia. Finally, U.S. Pat. No. 5,536,412 B1 discloses hemofiltration and plasmafiltration devices in which blood flows through the interior of a hollow fiber membrane and during the flow of blood, a sorbent suspension is circulated against the exterior surfaces of the hollow fiber membrane. Another step involves having the plasma fraction of the blood alternately exit and re-enter the interior of the membrane thereby effectuating removal of toxins. The sorbent can be activated charcoal along with an ion-exchanger such as a zeolite or a cation-exchange resin.

There are problems associated with the adsorbents disclosed in the above patents. For example, charcoal does not remove any water, phosphate, sodium or other ions. Zeolites have the disadvantage that they can partially dissolve in the dialysis solution, allowing aluminum and/or silicon to enter the blood, directly or indirectly from the dialysate. Additionally, zeolites can adsorb sodium, calcium and potassium ions from the blood or dialysate thereby requiring that these ions be added back into the blood or dialysate. It is also known that zeolites only exchange cations and thus in order to remove phosphate anions a separate anion exchanger is required in order to keep the phosphorus concentration between desired levels. One system currently in use is the REDY™ Sorbent System which consists of a cartridge containing five layers or beds. The first layer is an activated carbon layer to remove heavy metals, the second layer is an urease layer which converts urea to ammonium carbonate, the third layer is a zirconium phosphate layer which removes cations such as ammonium ions, the fourth layer is a hydrous zirconium oxide layer which remove anions such as phosphates and finally the fourth layer is another activated carbon layer which removes organic metabolites such as creatinine.

Applicants have developed a process and composition which both simplifies the above described systems, e.g. REDY™ Sorbent System and has better performance without some of the disadvantages of the referenced art. The process involves using an ion exchange composite comprising a mixture of a microporous cation exchange composition and an anion exchange composition. Carbon beds can also be used in front of and in back of the ion exchange composite. A urease bed is also used in the case of dialysate solution. The microporous cation exchange compositions have an empirical formula on an anhydrous basis of:

$$A_pM_xZr_{1-x}Si_nGe_yO_m \tag{I}$$

or $$A_pM_xTi_{1-x}Si_nGe_yO_m \tag{II}$$

where A is an exchangeable cation selected from the group consisting of potassium ion, sodium ion, rubidium ion, cesium ion, calcium ion, magnesium ion, hydronium ion or mixtures thereof, M is at least one framework metal selected from the group consisting of hafnium (4+), tin (4+), niobium (5+), titanium (4+), cerium (4+), germanium (4+), praseodymium (4+), and terbium (4+), except that M is not titanium in formula (II), "p" has a value from about 1 to about 20, "x" has a value from zero to less than 1, "n" has a value from 0 to about 12, "y" has a value from 0 to about 12, "m" has a value from about 3 to about 36 and $1 \leq n+y \leq 12$. The germanium can substitute for the silicon, zirconium/titanium or combinations thereof. Examples of the anionic exchange compositions are hydrous zirconium oxide and zirconia.

SUMMARY OF THE INVENTION

This invention relates to a composition and a process for removing contaminants from a fluid. Accordingly, one embodiment of the invention is a process for removing toxins from a fluid selected from the group consisting of blood and a dialysate solution, the process comprising directly or indirectly contacting the fluid with a shaped ion exchange composite at ion exchange conditions thereby providing a purified fluid, the composite comprising a mixture of a microporous cation exchange composition and an anion exchange composition, where the cation exchange composition is selected from the group consisting of zirconium metallate, titanium metallate and mixtures thereof, the metallates respectively having an empirical formula on an anhydrous basis of:

$$A_pM_xZr_{1-x}Si_nGe_yO_m \quad (I)$$

or

$$A_pM_xTi_{1-x}Si_nGe_yO_m \quad (II)$$

where A is an exchangeable cation selected from the group consisting of potassium ion, sodium ion, calcium ion, magnesium and mixtures thereof, M is at least one framework metal selected from the group consisting of hafnium (4+), tin (4+), niobium (5+), titanium (4+), cerium (4+), germanium (4+), praseodymium (4+), and terbium (4+), except that M is not titanium in formula (II), "p" has a value from about 1 to about 20, "x" has a value from zero to less than 1, "n" has a value from 0 to about 12, "y" has a value from 0 to about 12, "m" has a value from about 3 to about 36 and $1 \leq n+y \leq 12$, and the anion exchange composition is selected from the group consisting of hydrous zirconium oxide, zirconia, alumina, titania, hydrous titanium oxide, layered double hydroxides, single phase metal oxide solid solutions, magnesium hydroxide, calcium hydroxide, silica, amorphous mixed metal oxides, basic clays and mixtures thereof.

This and other objects and embodiments will become clearer after a detailed description of the invention.

DETAILED DESCRIPTION OF THE INVENTION

Applicants have developed an ion exchange composite and a process for removing toxins from blood or dialysate solutions using the composite. One essential element of applicants' composite is a microporous cation exchange composition. Cation exchange compositions are well known in the art and are defined as compositions which contain cations that can be exchanged with other cations without altering the structure of the composition. Zeolites and non-zeolitic molecular sieves are examples of cation exchangers.

Applicants have determined that microporous compositions identified as zirconium metallate and titanium metallate compositions have a large capacity for ammonium cations. The microporous compositions are described in U.S. Pat. No. 5,891,417 B1 and U.S. Pat. No. 6,099,737 B1 both of which are incorporated by reference.

These compositions are further identified by their empirical formulas (on an anhydrous basis) which respectively are:

$$A_pM_xZr_{1-x}Si_nGe_yO_m \quad (I)$$

or

$$A_pM_xTi_{1-x}Si_nGe_yO_m \quad (II)$$

In the case of formula I, the composition has a microporous framework structure composed of $ZrO_3$ octahedral units and at least one of $SiO_2$ tetrahedral units and $GeO_2$ tetrahedral units. In the case of formula II, the microporous framework structure is composed of $TiO_3$ octahedral units and at least one of $SiO_2$ tetrahedral units and $GeO_2$ tetrahedral units.

In both formulas I and II, A is an exchangeable cation selected from the group consisting of potassium ion, sodium ion, rubidium ion, cesium ion, calcium ion, magnesium ion, hydronium ion or mixtures thereof, M is at least one framework metal selected from the group consisting of hafnium (4+), tin (4+), niobium (5+), titanium (4+), cerium (4+), germanium (4+), praseodymium (4+), and terbium (4+), "p" has a value from about 1 to about 20, "x" has a value from zero to less than 1, "n" has a value from 0 to about 12, "y" has a value from 0 to about 12, "m" has a value from about 3 to about 36 and the sum of n+y has a value from about 1 to about 12. That is $1 \leq n+y \leq 12$. In equation (II) M is, of course, not titanium. The M metals which can be inserted into the framework in place of zirconium will be present as $MO_3$ octahedral units and thus it is a requirement that they are capable of being octahedrally coordinated. The germanium can be inserted into the framework in place of silicon and will be present as $MO_2$ tetrahedral units. Additionally, germanium can be inserted into the framework as a $MO_3$ octahedral unit replacing some of the zirconium in formula (I) or some of the titanium in formula (II). That is, germanium can replace some or all of the silicon, some of the zirconium in formula (I), some of the titanium in formula (II) or both silicon and zirconium or both silicon and titanium.

The zirconium metallates are prepared by a hydrothermal crystallization of a reaction mixture prepared by combining a reactive source of zirconium, silicon and/or germanium, optionally one or more M metal, at least one alkali metal and water. The alkali metal acts as a templating agent. Any zirconium compound, which can be hydrolyzed to zirconium oxide or zirconium hydroxide, can be used. Specific examples of these compounds include zirconium alkoxide, e.g., zirconium n-propoxide, zirconium hydroxide, zirconium acetate, zirconium oxychloride, zirconium chloride, zirconium phosphate and zirconium oxynitrate. The sources of silica include colloidal silica, fumed silica and sodium silicate. The sources of germanium include germanium oxide, germanium alkoxides and germanium tetrachloride. Alkali sources include potassium hydroxide, sodium hydroxide, rubidium hydroxide, cesium hydroxide, sodium carbonate, potassium carbonate, rubidium carbonate, cesium carbonate, sodium halide, potassium halide, rubidium halide, cesium halide, sodium ethylenediamine tetraacetic acid (EDTA), potassium EDTA, rubidium EDTA, and cesium EDTA. The M metals sources include the M metal oxides, alkoxides, halide salts, acetate salts, nitrate salts and sulfate salts. Specific examples of the M metal sources include, but are not limited to titanium alkoxides, titanium tetrachloride, titanium trichloride, titanium dioxide, tin tetrachloride, tin isopropoxide, niobium isopropoxide, hydrous niobium oxide, hafnium isopropoxide, hafnium chloride, hafnium oxychloride, cerium chloride, cerium oxide and cerium sulfate.

The titanium metallates are prepared in an analogous manner to the zirconium metallates. Thus, the sources of silicon, germanium, M metal and alkali metal are as enumerated above. The titanium source is also as enumerated above, namely titanium alkoxides, titanium tetrachloride, titanium trichloride and titanium dioxide. A preferred titanium source is titanium alkoxides with specific examples being titanium isopropoxide, titanium ethoxide and titanium butoxide.

Generally, the hydrothermal process used to prepare the zirconium metallate or titanium metallate ion exchange compositions involves forming a reaction mixture which in terms of molar ratios of the oxides is expressed by the formulae:

$$aA_2O:bMO_{q/2}:1-bZrO_2:cSiO_2:dGeO_2:eH_2O \tag{III}$$

and $$aA_2O:bMO_{q/2}:1-bTiO_2:cSiO_2:dGeO_2:eH_2O \tag{IV}$$

where "a" has a value from about 0.25 to about 40, "b" has a value from 0 to about 1, "q" is the valence of M, "c" has a value from about 0.5 to about 30, "d" has a value from 0 to about 30 and "e" has a value of 10 to about 3000. The reaction mixture is prepared by mixing the desired sources of zirconium, silicon and optionally germanium, alkali metal and optional M metal in any order to give the desired mixture. It is also necessary that the mixture have a basic pH and preferably a pH of at least 8. The basicity of the mixture is controlled by adding excess alkali hydroxide and/or basic compounds of the other constituents of the mixture. Having formed the reaction mixture it is next reacted at a temperature of about 100° C. to about 250° C. for a period of about 1 to about 30 days in a sealed reaction vessel under autogenous pressure. After the allotted time, the mixture is filtered to isolate the solid product which is washed with deionized water and dried in air.

As stated the microporous compositions have a framework structure of octahedral $ZrO_3$ units, at least one of tetrahedral $SiO_2$ units and tetrahedral $GeO_2$ units and optionally octahedral $MO_3$ units. This framework results in a microporous structure having an intracrystalline pore system with uniform pore diameters, i.e., the pore sizes are crystallographically regular. The diameter of the pores can vary considerably from about 3 Å and larger.

As synthesized, the microporous compositions will contain some of the alkali metal templating agent in the pores. These metals are described as exchangeable cations, meaning that they can be exchanged with other (secondary) A' cations. Generally, the A exchangeable cations can be exchanged with A' cations selected from other alkali metal cations ($K^+$, $Na^+$, $Rb^+$, $Cs^+$), alkaline earth cations ($Mg^{2+}$, $Ca^{2+}$, $Sr^{2+}$, $Ba^{2+}$), hydronium ion or mixtures thereof. It is understood that the A' cation is different from the A cation. The methods used to exchange one cation for another are well known in the art and involve contacting the microporous compositions with a solution containing the desired cation (at molar excess) at exchange conditions. Exchange conditions include a temperature of about 25° C. to about 100° C. and a time of about 20 minutes to about 50 hours. The particular cation (or mixture thereof) which is present in the final product will depend on the particular use and the specific composition being used. One specific embodiment is a cation exchange composition where the A' cation is a mixture of $Na^+$, $Ca^{+2}$ and $H^+$ ions.

These cation exchange compositions have been designated UZSi-n (see the '417 and '737 patents) where "n" is an integer which denotes a specific crystalline phase. Specific phases which are useful in the present invention include but are not limited to UZSi-1, UZSi-9 and UZSi-11.

Another essential component of the present invention is an anion exchange composition. Non-limiting examples of these anion exchange compositions are hydrous zirconium oxide, zirconia, alumina, titania, hydrous titanium oxide, layered double hydroxides (LDH), single phase metal oxide solids solutions (MOSS), magnesium hydroxide, calcium hydroxide, silica, amorphous mixed metal oxides, and basic clays. The preparation of these anion exchange compositions is well known in the art and some are commercially available. By single phase metal oxide solid solutions is meant mixtures of metal oxides which form a solid solution, i.e. one oxide "dissolved" in the other oxide but which have only one phase as shown by x-ray diffraction. One example of a MOSS is ceria/zirconia with varying ratios of Ce/Zr. Layered double hydroxides are compositions comprised of octahedral layers, i.e. the metal cations are octahedrally surrounded by hydroxyl groups. These octahedra share edges to form infinite sheets. Interstitial anions such as carbonate are present to balance the positive charge in the octahedral layers. One example of a LDH is hydrotalcite. U.S. Pat. No. 5,232,887 B1 and references cited therein, all of which incorporated by reference, present details on LDH including preparation procedures. Amorphous mixed metal oxides are chemical mixtures (not physical mixtures) of oxides which are x-ray amorphous. An example of these amorphous materials is amorphous silica-alumina, which is described in U.S. Pat. No. 3,909,450 B1, U.S. Pat. No. 3,274,124 B1 and U.S. Pat. No. 4,988,659 B1 all of which are incorporated by reference. Finally, examples of clays (without limitation) include halloysite, bentonite, montmorillonite, etc.

The cation and anion exchange compositions are next combined and formed into various shapes by means well known in the art. Non-limiting examples of these various shapes include pills, extrudates, spheres, pellets and irregularly shaped particles. Although the microporous compositions can be formed into shaped articles without using a binder, it is preferred to use a binder. The binders which can be used are well known and include alumina, silica, amorphous silica/alumina, hydrous zirconium oxide, zirconia, zirconium phosphate, alumina, aluminum phosphate, titania, titanium phosphate, hydrous titanium oxide, layered double hydroxides, magnesium hydroxide, calcium hydroxide, silica, basic clays and mixtures thereof. Again the process of preparing shaped articles using a binder is well known in the art. For example, the desired binder can be peptized with an acid such as nitric acid or hydrochloric acid and then combined with the cation and anion exchange compositions, formed into the desired shape and finally calcined to form a shaped article. Since the binder materials include many of the anion exchange compositions, one can use the same binder as the anion exchanger or a binder which is different from the anion exchanger. If the binder is the same as the anion exchanger, one can peptize the entire amount of anion exchanger and then convert it to the oxide or use a portion in the oxide form and a portion which is peptized and used as a binder.

A particular procedure which can be used when the binder is hydrous zirconium oxide or hydrous titanium oxide is described in U.S. Pat. No. 6,099,737 B1 which is incorporated by reference. This procedure is described here for completeness. The process uses a binder precursor which when heated as described below will be converted to a hydroxy zirconium or titanium oxide binder. The binder precursors are metal compounds which can form a gel by changing its pH. Examples of the binder precursors which can be used, include but are not limited to zirconium tetrapropoxide, zirconium acetate solution, zirconyl hydroxychloride, zirconyl oxychloride, zirconyl orthosulfate, zirconyl oxynitrate, and the titanium analogs of the above named compounds.

Generally the binder precursor is conveniently mixed with water, to which the desired cation and anion exchange compositions are added or vice versa to form a mixture. The amount of precursor in the mixture can vary considerably, but is generally the amount necessary to give from about 10 to about 50 wt. % of hydroxy metal oxide in the finished shaped article. The resultant mixture is homogeneously mixed by means well know in the art such as mulling, kneading, shearing, stirring, etc. Water is usually added to the mixture before or during mixing to obtain the appropriate consistency required for the desired forming means. The amount of water which is added will also determine the type of mixing means to be used.

Since the binder precursor undergoes gelation during preparation of the shaped article, it is important to control the gelation rate of the precursor. Failure to control the gelation rate can result in an inhomogeneous mixture of the binder and cation plus anion exchange compositions or result in the binder/composition mixture being turned into an unworkable mass. For example, a large or drastic shift in pH can occur when very basic cation plus anion exchange compositions are mixed with a very acidic binder precursor. Examples of these very basic compositions are alkali silicotitanates, or alkali metallogermanates, while clays are only slightly basic.

If it is found that the cation plus anion exchange compositions are too basic and cause premature gelation, they can be treated to reduce the basicity. This can be done by treating the mixed composition with an acid solution such as nitric acid, hydrochloric acid, etc., and used directly in the formulation or, alternatively, followed by filtration and washing with water. This procedure is carried out until the resultant acid washed cation plus anion exchange composition when mixed with the binder precursor gives a homogeneous and workable mixture or slurry.

An alternative way to prepare a mixture of the binder precursor and cation plus anion exchange composition is to first gel the precursor and then mix it with the composition. One convenient manner of gelling the binder precursor is by preparing an aqueous solution of base such as sodium hydroxide, potassium hydroxide, etc. and adding the binder precursor to it. The resultant slurry is filtered, the solid washed and then mixed with the desired cation plus anion exchange compositions. When preparing an article using the gelled binder precursor and a very basic cation plus anion exchange composition, it is not necessary to treat the cation plus anion exchange composition with an acid, although it is preferred to do so.

Having obtained a homogeneous mixture, it is now formed into a desired shape by forming means well know in the art. These forming means include extrusion, spray drying, oil dropping, conical screw mixing, etc. Extrusion means include screw extruders and extrusion presses. As mentioned above, the forming means will determine how much water, if any, is added to the mixture. Thus if extrusion is used, then the mixture should be in the form of a dough, whereas if spray drying or oil dropping is used, then enough water needs to be present in order to form a slurry. Note that these forming steps can be used for any binder.

Having formed the mixture into a desired article, it is next heated at temperatures of about 85° C. to about 120° C. Heating at these low temperatures sets the binder but does not convert it to the oxide. Therefore, one obtains a shaped article comprising a cation and anion exchange compositions and a hydroxy metal oxide binder. By a hydroxy metal oxide is meant an oxide having the empirical formula $MO_2 \cdot xH_2O$, where x ranges from about 2 to about 4 and M is zirconium or titanium. They hydroxy metal oxide is x-ray amorphous or poorly crystalline.

Although the preferred embodiment is to have shaped articles containing both an anion and a cation exchange composition, the two exchange compositions can be present as separate articles (prepared as above) which can then be physically mixed or be in separate beds.

The composite of the invention is used in a process for removing toxins from blood (directly or indirectly) or a dialysate solution. The process involves contacting the fluid, i.e. blood or dialysate, at ion exchange conditions thereby removing at least a portion of the toxins. Ammonium ion is the most common cation toxin which must be removed.

In the event of liver failure, ammonium ions will be present in the blood and contact with the composites of the invention will reduce or substantially remove the ammonium ions. The contacting can be carried out by means known in the art (see, Background of the Invention above). One way to carry out the process is to first contact the blood with a dialysate solution and then contact the dialysate with shaped particles of the composite and re-circulate the dialysate to further contact the blood. This process is advantageous over a once through process because it uses considerably less amounts of dialysate. Direct contact of the blood with the composite can also be carried out since the composites of the invention are essentially insoluble in blood.

In the case of renal failure, the blood is first contacted with a dialysate to remove uremic substances, e.g. urea, from the blood. The dialysate is then regenerated and recirculated. Regeneration is carried out by contacting the urea containing dialysate with urease to convert the urea to ammonium ion and carbonate ion according to the equation:

$$2H_2O + H_4N_2CO \rightarrow 2NH_4^+ + CO_3^= \qquad (I)$$

When urease is needed to carry out reaction (I), it can be present in the process as a component of the composite, i.e. immobilized on the composite, immobilized on a separate support, present as an unsupported material or be present in the dialysate. Details regarding bonding of urease to microporous compositions can be found in U.S. Pat. No. 4,581,141 B1 which is incorporated by reference.

By removing ammonium ions, reaction (I) can proceed to the right. The carbonate can be removed by forming salts with cations such as potassium, sodium, calcium, etc. which are either present in the starting solution (before contact with the composite) or are present on the cation exchange compositions and are exchanged for the ammonium ions.

As described above in detail, the composite of the invention also contains an anion exchange composition. The reason for this anion exchange composition is to remove phosphorous (as phosphate, $PO_4^=$) from the fluid in order to maintain the phosphorus level within desirable limits. See, Handbook of Dialysis, J. T. Dougirdas, T. S. Ing editors, $2^{nd}$ edition, 1994, Little Brown and Company, pp. 510–511. By combining the cation exchange composition with the anion exchange composition in one shaped article, applicants have substantially simplified the process of removing both cationic and anionic toxins from blood or dialysate.

The process can be run in a number of physical configurations. For example, in one configuration the ion exchange composite can be present as a fixed bed through which the desired fluid is flowed either upflow or downflow. Urease can be immobilized on the composite or can be present as a separate bed, either supported or unsupported, immediately preceding the ion exchange bed. Optionally a carbon bed can be used before the urease bed and/or after the ion-exchange bed. Another configuration is to use the composite in the form of a slurry which would contact the fluid via a permeable membrane. Urease can be present in the slurry. The conditions for carrying out the process are known in the art and include a contact time sufficient to remove at least a portion of the toxins and a temperature compatible with the fluid being treated.

In order to more fully illustrate the invention, the following examples are set forth. It is to be understood that the examples are only by way of illustration and are not intended as an undue limitation on the broad scope of the invention as set forth in the appended claims.

EXAMPLE 1

A solution was prepared by mixing 4150 g of sodium silicate, 484 g of sodium hydroxide and 1909 g $H_2O$. After several minutes of vigorous stirring 2458 g zirconium acetate solution (22.1 wt. % $ZrO_2$) was added. This was stirred for an additional 15 minutes and the resulting gel was transferred to a stainless steel reactor and stirred for 72 hours at 200° C. The reactor was cooled to room temperature and the mixture was vacuum filtered to isolate solids which were washed with deionized water and dried in air. The solid reaction product was analyzed and found to contain 16.72 wt. % $Na_2O$, 51.98 wt. % $SiO_2$, 30.93 wt. % $ZrO_2$, LOI 10.8 wt. %, which gives a formula of $Na_{2.15}ZrSi_{3.45}O_{9.97} \cdot 2.68H_2O$. This product was identified as UZSi-9 by powder XRD and labeled sample A.

EXAMPLE 2

To a vessel there were mixed 458 g of sample A and 355 g of water to provide a slurry with a pH of about 13. Glacial acetic acid was added slowly to reach a final slurry pH of about 6.

The above slurry was added to a container, which was chilled to about 10 to 15° C. To this slurry there were added 350 g of zirconyl acetate which had been chilled to 10 to 15° C. and the resultant slurry was stirred vigorously. Next the slurry was spray dried to provide 20 to 50 micron diameter particles.

EXAMPLE 3

A mixture of 70 g of zirconyl nitrate and 13 g of water was added to a container, to which there were added 29 ml of a 20 wt. % sodium hydroxide solution to give a soft gel. The gel along with 89 g of sample A were added to a muller and the mixture mulled for 30 minutes. Next, 10 g of water and 2 g of glycerin were added, the mixture mulled for an additional 10 minutes and then extruded using a piston extruder. The extrudates were dried at room temperature overnight and then calcined at 200° C. for two hours. Finally, the extrudates were crushed to give particles of about 250 to about 420 microns in diameter. This sample was identified as sample H-1.

EXAMPLE 4

One half of the H-1 sample was further crushed to provide a powder comprised of particles of less than 50 microns in diameter. This sample was identified as sample H-2.

EXAMPLE 5

Extrudates were prepared by first mulling 276 g of sample A. To the muller, 87 g of magnesium hydroxide ($Mg(OH)_2$) were added and the resultant mixture kneaded for 10 minutes. Next, 373 g of water were added to increase the extrudability of the dough and mulling was continued for an additional 30 minutes. The mixture was extruded on a piston extruder using a 1.78 mm die plate. The resultant extrudates were dried overnight under ambient conditions and then heated at 200° C. for two hours. The dried extrudates were next crushed to give particles of about 250 to about 600 microns in diameter. This sample was identified as sample M.

EXAMPLE 6

Samples A, H-1, H-2 and M were tested for removal of ammonium and phosphate ions using the following procedure. A test solution was prepared by mixing 28.6 ml of a dialysate concentrate with 971 ml of deionized water, 2.675 g of ammonium chloride ($NH_4Cl$) and 0.446 g of monobasic monhydrate sodium phosphate ($NaH_2PO_4H_2O$). The final composition of the dialysate test solution is shown in Table 1.

TABLE 1

Dialysate Test Solution Composition

| Element | wt. % |
|---------|-------|
| Na | 0.314 |
| Ca | 0.0049 |
| K | 0 |
| Mg | 0.0018 |
| $NH_4$ | 0.105 |
| P | 0.0107 |

Into a 25 ml vial, there were added 200 mg of the sample to be tested, to which there were added 10 ml of the above test dialysis solution. The vial was placed in an upright shaker and agitated at room temperature for 24 hours. The mixture was then filtered and the filtrate analyzed for $NH_4^+$ and phosphorous. The results for these samples are presented in Table 2.

TABLE 2

Removal of Dialysate Components by Various Compositions

| | Amount of Component Removal (%) | |
|---|---|---|
| Sample ID | $NH_4$ | Phosphorus |
| A | 91.5 | 5.6 |
| H-1 | 86.7 | 100 |
| H-2 | 87.6 | 100 |
| M | 82.9 | 100 |
| $ZrPO_4$* | 61.0 | 0[1] |
| $ZrO_2$* | 6.7 | 100 |

*Obtained from a commercial Redy ™ cartridge
[1]product analysis similar to feed The results in Table 2 show that the composites of the invention are able to remove both ammonium and phosphorous ions better than conventional materials. Note that the amount of UZSi-9 in samples H-1, H-2 and M are less than the amount (weight) of $ZrPO_4$ or the pure UZSi-9 (sample A). Additionally, the amount of $ZrO_2$ in the H-1 or H-2 samples is less than in the pure $ZrO_2$. Surprisingly, samples H-1 and H-2 have substantially similar performance to the pure components while using smaller amounts of materials.

What is claimed is:

1. A process for removing toxins from a fluid selected from the group consisting of blood and a dialysate solution, the process comprising directly or indirectly contacting the fluid with a shaped ion exchange composite at ion exchange conditions thereby providing a purified fluid, the composite comprising a mixture of a microporous cation exchange composition and an anion exchange composition, where the cation exchange composition is selected from the group consisting of zirconium metallate, titanium metallate and mixtures thereof, the metallates respectively having an empirical formula on an anhydrous basis of:

$$A_pM_xZr_{1-x}Si_nGe_yO_m \quad (I)$$

or $$A_pM_xTi_{1-x}Si_nGe_yO_m \quad (II)$$

where A is an exchangeable cation selected from the group consisting of potassium ion, sodium ion, calcium ion, magnesium ion and mixtures thereof, M is at least one framework metal selected from the group consisting of hafnium (4+), tin (4+), niobium (5+), titanium (4+), cerium (4+), germanium (4+), praseodymium (4+), and terbium (4+), except that M is not titanium in formula (II), "p" has a value from about 1 to about 20, "x" has a value from zero to less than 1, "n" has a value from 0 to about 12, "y" has a value from 0 to about 12, "m" has a value from about 3 to about 36 and $1 \leq n+y \leq 12$, and the anion exchange composition is selected from the group consisting of hydrous zirconium oxide, zirconia, alumina, titania, hydrous titanium oxide, layered double hydroxides, single phase metal oxide solid solutions, magnesium hydroxide, calcium hydroxide, silica, amorphous mixed metal oxides, basic clays and mixtures thereof.

2. The process of claim 1 where the fluid is blood.

3. The process of claim 1 where the fluid is a dialysate solution.

4. The process of claim 1 where the ion exchange composite is contained in a fixed bed.

5. The process of claim 1 where the ion exchange composite is in a shape selected from the group consisting of extrudates, pills, pellets, spheres and irregularly shaped particles.

6. The process of claim 1 where the composite is further characterized in that it contains a binder selected from the group consisting of hydrous zirconium oxide, zirconia, zirconium phosphate, alumina, aluminum phosphate, titania, titanium phosphate, hydrous titanium oxide, layered double hydroxides, magnesium hydroxide, calcium hydroxide, silica, basic clays and mixtures thereof.

7. The process of claim 1 further characterized in that the fluid is contacted with urease before being contacted with the ion exchange composite.

8. The process of claim 7 further characterized in that the fluid is contacted with a carbon bed prior to being contacted with the urease and the purified fluid is contacted with a carbon bed.

9. The process of claim 1 where the toxin is ammonium ion.

10. The process of claim 1 where the toxins are ammonium and phosphate ions.

11. The process of claim 1 where M is tin (4+).

12. The process of claim 1 where M is titanium (4+).

13. The process of claim 1 where M is niobium (5+).

14. The process of claim 1 where n=0.

15. The process of claim 1 further characterized in that the A cation is exchanged for a different secondary cation, A', selected from the group consisting of alkali metals, alkaline earth metal, hydronium ions and mixtures thereof.

16. The process of claim 15 where A' is a mixtures of sodium and calcium ions.

17. The process of claim 15 where A' is a mixture of sodium, calcium and hydronium ions.

18. The process of claim 1 where the cation exchange composition has the structure of UZSi-9, UZSi-11 or UZSi-1.

19. A shaped ion exchange composite for removing toxins from blood or dialysate the composite comprising a mixture of a microporous cation exchange composition and an anion exchange composition, where the cation exchange composition is selected from the group consisting of zirconium metallate, titanium metallate and mixtures thereof, the metallates respectively having an empirical formula on an anhydrous basis of:

$$A_pM_xZr_{1-x}Si_nGe_yO_m \quad (I)$$

or $$A_pM_xTi_{1-x}Si_nGe_yO_m \quad (II)$$

where A is an exchangeable cation selected from the group consisting of potassium ion, sodium ion, calcium ion, magnesium ion and mixtures thereof, M is at least one framework metal selected from the group consisting of hafnium (4+), tin (4+), niobium (5+), titanium (4+), cerium (4+), germanium (4+), praseodymium (4+), and terbium (4+), except that M is not titanium in formula (II), "p" has a value from about 1 to about 20, "x" has a value from zero to less than 1, "n" has a value from 0 to about 12, "y" has a value from 0 to about 12, "m" has a value from about 3 to about 36 and $1 \leq n+y \leq 12$, and the anion exchange composition is selected from the group consisting of hydrous zirconium oxide, zirconia, alumina, titania, hydrous titanium oxide, layered double hydroxides, single phase metal oxide solid solutions, magnesium hydroxide, calcium hydroxide, silica, amorphous mixed metal oxides, basic clays and mixtures thereof.

20. The composite of claim 19 where the ion exchange composite is in a shape selected from the group consisting of extrudates, pills, pellets, spheres and irregularly shaped particles.

21. The composite of claim 19 further characterized in that it contains a binder selected from the group consisting of hydrous zirconium oxide, zirconia, zirconium phosphate, alumina, aluminum phosphate, titania, titanium phosphate, hydrous titanium oxide, layered double hydroxides, magnesium hydroxide, calcium hydroxide, silica, basic clays and mixtures thereof.

22. The composite of claim 19 where M is tin (4+).

23. The composition of claim 19 where M is titanium (4+).

24. The composition of claim 19 where M is niobium (5+).

25. The composition of claim 19 where n=0.

26. The composition of claim 19 further characterized in that the A cation is exchanged for a different secondary cation, A', selected from the group consisting of alkali metals, alkaline earth metal, hydronium ions and mixtures thereof.

27. The composition of claim 26 where A' is a mixtures of sodium and calcium ions.

28. The composition of claim 26 where A' is a mixture of sodium, calcium and hydronium ions.

29. The composition of claim 19 where the cation exchange composition has the structure of UZSi-9, UZSi-11 or UZSi-1.

* * * * *